US 6,635,056 B2

(12) United States Patent
Kadhiresan et al.

(10) Patent No.: US 6,635,056 B2
(45) Date of Patent: Oct. 21, 2003

(54) RF ABLATION APPARATUS AND METHOD USING AMPLITUDE CONTROL

(75) Inventors: Veerichetty A. Kadhiresan, Temecula, CA (US); Jeffrey A. Hall, Birmingham, AL (US); David S. Wood, Temecula, CA (US); Kathryn Kasischke, San Diego, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 54 days.

(21) Appl. No.: 09/974,465

(22) Filed: Oct. 9, 2001

(65) Prior Publication Data

US 2003/0069573 A1 Apr. 10, 2003

(51) Int. Cl.[7] .............................................. A61B 18/18
(52) U.S. Cl. ........................................................ 606/34
(58) Field of Search .......................... 606/32–35, 40–42

(56) References Cited

U.S. PATENT DOCUMENTS

| 5,370,645 A | * | 12/1994 | Klicek et al. | 606/35 |
| 5,383,917 A | | 1/1995 | Desai et al. | |
| 5,472,443 A | * | 12/1995 | Cordis et al. | 606/48 |
| 5,540,681 A | * | 7/1996 | Strul et al. | 606/34 |
| 5,637,090 A | | 6/1997 | McGee et al. | |
| 5,810,802 A | | 9/1998 | Panescu et al. | |
| 5,837,001 A | | 11/1998 | Mackey | |
| 6,001,093 A | | 12/1999 | Swanson et al. | |
| 6,059,778 A | * | 5/2000 | Sherman | 606/34 |
| 6,200,314 B1 | | 3/2001 | Sherman | |

* cited by examiner

Primary Examiner—Michael Peffley
(74) Attorney, Agent, or Firm—Fulwider Patton Lee & Utecht, LLP

(57) ABSTRACT

Power signals having controllable peak-to-peak amplitudes are provided to electrode sets so that during a first period of time, a first amplitude signal is provided to a first electrode set and a second amplitude signal is provided to a second electrode set. The first amplitude is greater than the second amplitude and bipolar current flows from the first electrode set to the second electrode set. During a second period of time, a third amplitude signal is provided to the first electrode set and a fourth amplitude signal is provided to the second electrode set. The third amplitude is less than the fourth amplitude and the current flows from the second electrode set to the first electrode set. Alternating first and second periods of time establish repetitive bipolar current flow between electrode sets. The addition of a backplate establishes unipolar current flow.

64 Claims, 8 Drawing Sheets

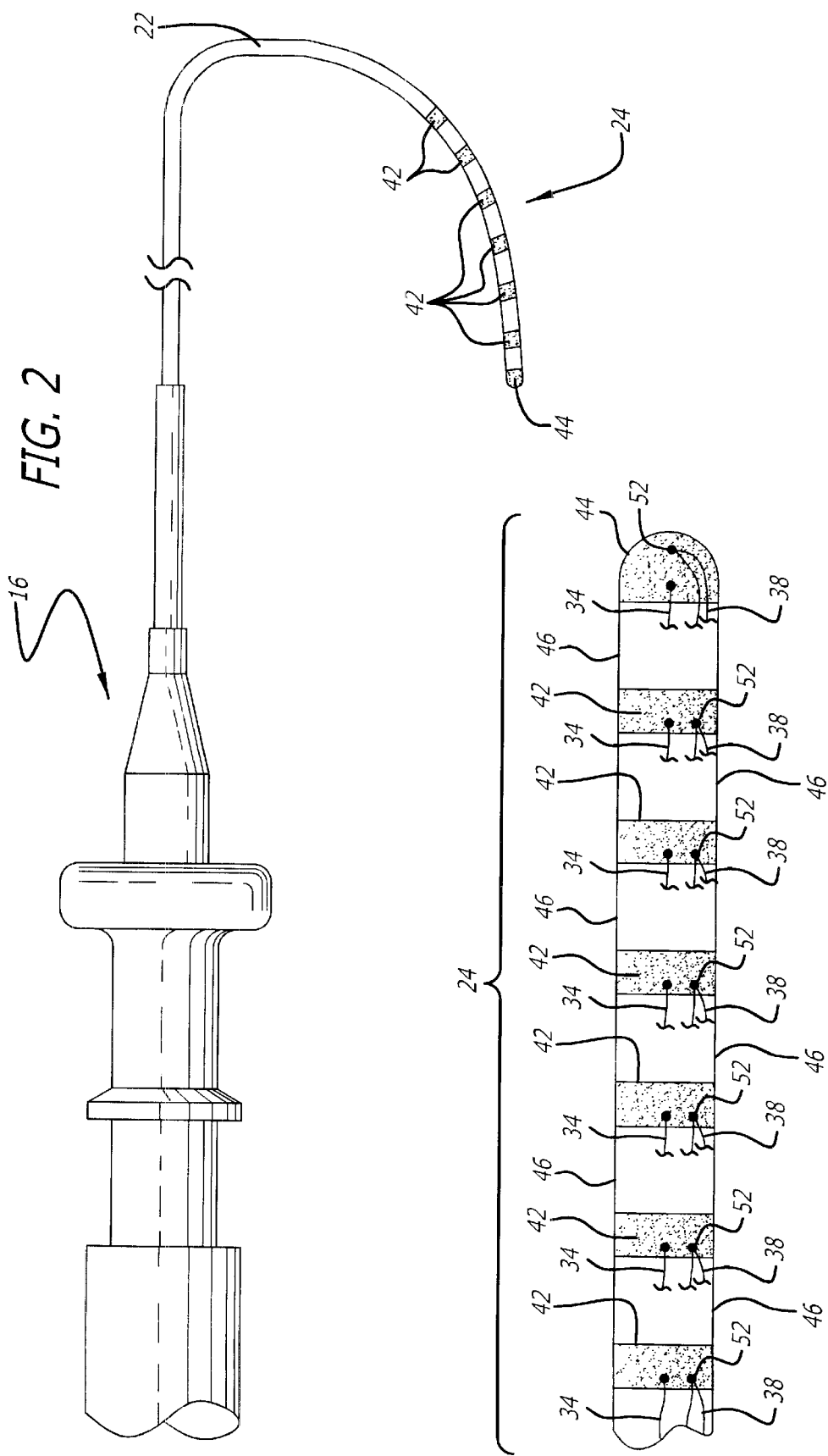

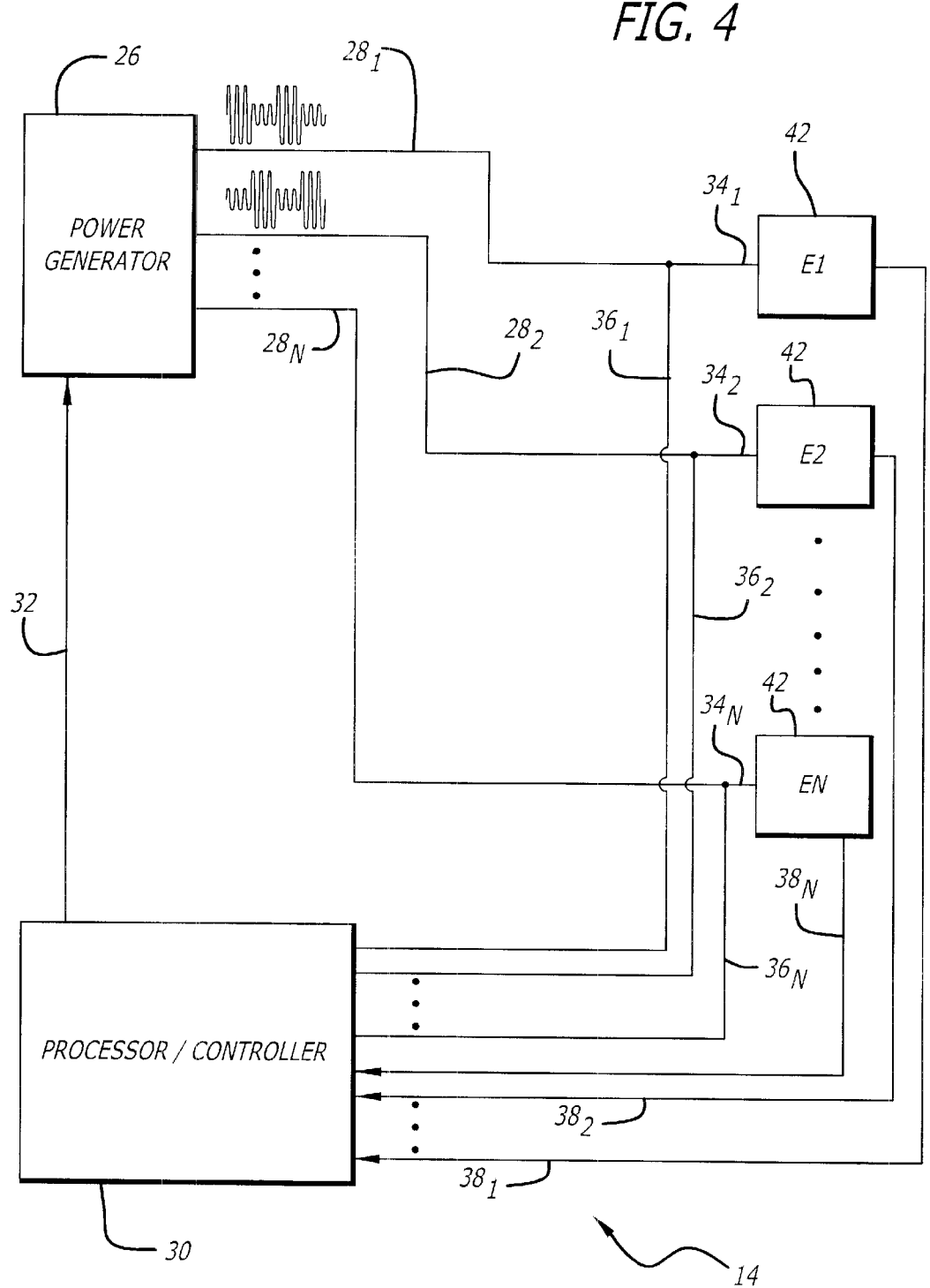

RF ABLATION APPARATUS AND METHOD USING AMPLITUDE CONTROL

BACKGROUND OF THE INVENTION

1. Field of the Invention

The invention relates generally to an electrophysiological ("EP") apparatus and method for providing energy to biological tissue and, more particularly, to a radio frequency ("RF") ablation apparatus for controlling the flow of current through biological tissue so that the depth and continuity of ablation lesions may be controlled.

2. Description of the Related Art

The heart beat in a healthy human is controlled by the sinoatrial node ("S-A node") located in the wall of the right atrium. The S-A node generates electrical signal potentials that are transmitted through pathways of conductive heart tissue in the atrium to the atrioventricular node ("A-V node") which in turn transmits the electrical signals throughout the ventricle by means of the His and Purkinje conductive tissues. Improper growth, remodeling, or damage to, the conductive tissue in the heart can interfere with the passage of regular electrical signals from the S-A and A-V nodes. Electrical signal irregularities resulting from such interference can disturb the normal rhythm of the heart and cause an abnormal rhythmic condition referred to as "cardiac arrhythmia."

While there are different treatments for cardiac arrhythmia, including the application of anti-arrhythmia drugs, in many cases ablation of the damaged tissue can restore the correct operation of the heart. Such ablation can be performed percutaneously, a procedure in which a catheter is introduced into the patient through an artery or vein and directed to the atrium or ventricle of the heart to perform single or multiple diagnostic, therapeutic, and/or surgical procedures. In such case, an ablation procedure is used to destroy the tissue causing the arrhythmia in an attempt to remove the electrical signal irregularities or create a conductive tissue block to restore normal heart beat. Successful ablation of the conductive tissue at the arrhythmia initiation site usually terminates the arrhythmia or at least moderates the heart rhythm to acceptable levels. A widely accepted treatment for arrhythmia involves the application of RF energy to the conductive tissue.

In the case of atrial fibrillation ("AF"), a procedure published by Cox et al. and known as the "Maze procedure" involves the formation of continuous atrial incisions to prevent atrial reentry and to allow sinus impulses to activate the entire myocardium. While this procedure has been found to be successful, it involves an intensely invasive approach. It is more desirable to accomplish the same result as the Maze procedure by use of a less invasive approach, such as through the use of an appropriate EP catheter system providing RF ablation therapy. In this therapy, transmural ablation lesions are formed in the atria to prevent atrial reentry and to allow sinus impulses to activate the entire myocardium. In this sense transmural is meant to include lesions that pass through the atrial wall or ventricle wall from the interior surface (endocardium) to the exterior surface (epicardium).

There are two general methods of applying RF energy to cardiac tissue, unipolar and bipolar. In the unipolar method a large surface area electrode; e.g., a backplate, is placed on the chest, back or other external location of the patient to serve as a return. The backplate completes an electrical circuit with one or more electrodes that are introduced into the heart, usually via a catheter, and placed in intimate contact with the aberrant conductive tissue. In the bipolar method, electrodes introduced into the heart have different potentials and complete an electrical circuit between themselves. In both the unipolar and the bipolar methods, the current traveling between the electrodes of the catheter and between the electrodes and the backplate enters the tissue and induces a temperature rise in the tissue resulting in ablation.

During ablation, RF energy is applied to the electrodes to raise the temperature of the target tissue to a lethal, non-viable state. In general, the lethal temperature boundary between viable and non-viable tissue is between approximately 45° C. to 55° C. and more specifically, approximately 48° C. Tissue heated to a temperature above 48° C. for several seconds becomes permanently non-viable and defines the ablation volume. Tissue adjacent to the electrodes delivering RF energy is heated by resistive heating which is conducted radially outward from the electrode-tissue interface. The goal is to elevate the tissue temperature, which is generally at 37° C., fairly uniformly to an ablation temperature above 48° C., while keeping both the temperature at the tissue surface and the temperature of the electrode below 100° C. In clinical applications, the target temperature is set below 70° C. to avoid coagulum formation. Lesion size has been demonstrated to be proportional to temperature.

A basic RF ablation system for forming linear lesions includes a catheter carrying a plurality of electrodes, a backplate and an RF generator adapted to provide RF signals to the electrodes to establish bipolar or unipolar current flow. In one such ablation system, as described in U.S. Pat. No. 6,200,314, RF signals having a constant amplitude and a controllable phase angle are supplied to each electrode. A backplate is maintained at a reference voltage level in relation to the amplitude of the RF signals. The power control system controls the relative phase angles of the RF signals to establish a voltage potential between the electrodes. Current thus flows between the electrodes and between the electrodes and the backplate to produce linear lesions. In order to establish the phase difference between RF signals, the system requires a programmable logic array and a controllable frequency source. The logic array receives phase control signals from a microprocessor and controls the frequency source accordingly.

In other, less complex RF ablation systems, such as those described in U.S. Pat. Nos. 5,810,802 and 6,001,093, a controller electrically couples an indifferent electrode, i.e., backplate, and each of several electrodes to a single RF source through a network of switches. Depending on the setting of its associated switch, an electrode may be set to either an energy emitting polarity, an energy receiving polarity or neither (inactive). Using the switches, the system may be configured so that current flows between the electrodes or between the electrodes and the backplate. The system, however, does not provide for simultaneous unipolar and bipolar operation, thus lesion depth and continuity characteristics may be inadequate. Moreover, since power to all electrodes is supplied by a single source, any type of power control using temperature feedback may prove ineffective. Specifically, any power adjustments resulting from the operating conditions of one electrode, e.g., lower power due to an overheated electrode, necessarily affect the operating conditions of the remaining electrodes. This too can lead to inadequate lesion depth and continuity characteristics.

In other ablation systems having a generator with a limited number of output channels power delivery to some electrodes is not controllable. For example, as shown schematically in FIG. 13, for a six channel generator outputting power signals P1–P6 used in conjunction with a twelve band electrode catheter, every other electrode may be individually controlled while the remaining electrodes are maintained at a reference ground. Such a system has inherent problems with respect to temperature feedback power control. For example, if the temperature at electrode E2 increases above an acceptable threshold level, heat at electrode E2 is reduced by reducing the current flowing to it from adjacent electrodes E1 and E3. To accomplish this, power to electrode E1 may be shut off or reduced. If, however, the temperature at electrode E2 remains above the threshold, then the power to electrode E3 may have to be shut off or reduced. In this case little if any current flows between electrodes E1–E2 and electrodes E3–E2 and E3–E4. Thus electrodes E1 through E4 are effectively shut off due to an over-temperature condition at one electrode E2. As another example, if the temperature at electrode E4 increase above the threshold, power to electrode E3 may be shut off or reduced. This, however, affects the current path between E3 and E2. Such interdependence makes power control more difficult.

Hence, those skilled in the art have recognized a need for a multi-channel ablation system having independent power signal control capability for providing periodically fluctuating voltage potentials between electrodes to thereby induce unipolar and bipolar current flow through tissue without reliance on complex phasing circuitry. The need for a single channel ablation system having like power signal control capabilities for use in conjunction with multiple electrodes has also been recognized. The invention fulfills these needs and others.

SUMMARY OF THE INVENTION

Briefly, and in general terms, the invention is directed to sing e-channel and multi-channel ablation systems having controllable power signal capability for providing periodically fluctuating voltage potentials between electrodes to thereby establish unipolar or bipolar current flow through biological tissue.

In one aspect, the invention relates to a multi-channel system for ablating biological tissue using power signals having controllable peak-to-peak amplitudes. The system includes a catheter having a plurality of electrodes, a power generator that provides power signals to the electrodes and a processor that controls the power generator. The power generator is controlled so that during a first period of time, a first peak-to-peak amplitude signal is provided to at least one electrode defining a first electrode set and a second peak-to-peak amplitude signal is provided to at least one electrode defining a second electrode set. During the first period of time the first amplitude is greater than the second amplitude thereby establishing bipolar current flow from the first electrode set to the second electrode set. The power generator is also controlled so that during a second period of time, a third peak-to-peak amplitude signal is provided to the first electrode set and a fourth peak-to-peak amplitude signal is provided to the second electrode set. During this period of time the third amplitude is less than the fourth amplitude and current flows from the second electrode set to the first electrode set.

In a detailed aspect of the invention, the first amplitude signal and the third amplitude signal are provided by a first RF power signal while the second amplitude signal and the fourth amplitude signal are provided by a second RF power signal. The RF power signals may be continuous or duty cycled (pulsed). In a further detailed aspect the first and second RF power signals are in phase. In another detailed aspect, the processor controls the power generator so that there are a plurality of alternating first and second time periods during which any one of the first, second, third and fourth amplitudes may be varied to establish different levels of bipolar current flow between electrodes. In another detailed facet, the system includes a backplate. The power generator maintains the backplate at a reference voltage different then the peak-to-peak amplitude of any one of the first, second, third and fourth amplitudes, thereby establishing unipolar current flow between the electrodes and the backplate. In yet another detailed aspect of the invention, at least one electrode in each electrode set includes a temperature sensor or multiple temperature sensors that provide signals indicative of the temperature at the electrode to the processor. The processor converts the temperature signals to a temperature reading and compares the temperature reading to a target temperature. Based on the difference between the temperature reading and the target temperature, the processor adjusts the power provided to the electrode by the power signal.

In another aspect, the invention relates to a single channel system for ablating biological tissue using a power signal having a controllable peak-to-peak amplitude. The system includes a catheter having a plurality of electrode pairs and a power control system that establishes voltage potentials between the electrodes within an electrode pair. The power control system establishes a voltage potential between a first electrode pair during a first period of time by providing a first power signal to one of the electrodes while maintaining the other electrode at a reference potential. During a second period of time, the power control system establishes a voltage potential between a second electrode pair by providing the first power signal to one of the electrodes while maintaining the other electrode at the reference potential.

In a detailed facet of the invention, during subsequent time periods, the power control system establishes a voltage potential between each of the remaining electrode pairs by providing the first power signal to one of the electrodes while maintaining the other electrode at a reference potential. In another detailed aspect, the power control system repeatedly establishes voltage potentials between electrode pairs in sequence from the first electrode pair to the last electrode pair. In another detailed facet of the invention, the first and second electrode pairs comprise a common electrode and the first power signal is provided to the common electrode during each of the first and second time periods. In yet another detailed aspect of the invention, at least one electrode in each electrode pair includes a temperature sensor or multiple temperature sensors that provides signals indicative of the temperature at the electrode-tissue interface to the power control system. The power control system converts the temperature signals to a temperature reading and compares the temperature reading to a target temperature. Based on the difference between the temperature reading and the target temperature, the power control system adjusts the power provided to the electrode by the power signal.

These and other aspects and advantages of the invention will become apparent from the following detailed description and the accompanying drawings which illustrate by way of example the features of the invention.

BRIEF DESCRIPTION OF THE DRAWINGS

FIG. 2 is a diagram of the catheter system of FIG. 1 presenting more detail that includes a handle and a catheter sheath having a preformed distal segment carrying an electrode system;

FIG. 3a is a detailed schematic block diagram of one configuration of the electrode system of FIG. 2 having a tip electrode and several band electrodes arranged in a linear array;

FIG. 4 is a detailed block diagram of one configuration of the power control system of FIG. 1 employing a multi-channel power generator;

DETAILED DESCRIPTION OF THE PREFERRED EMBODIMENTS

Figure 1:
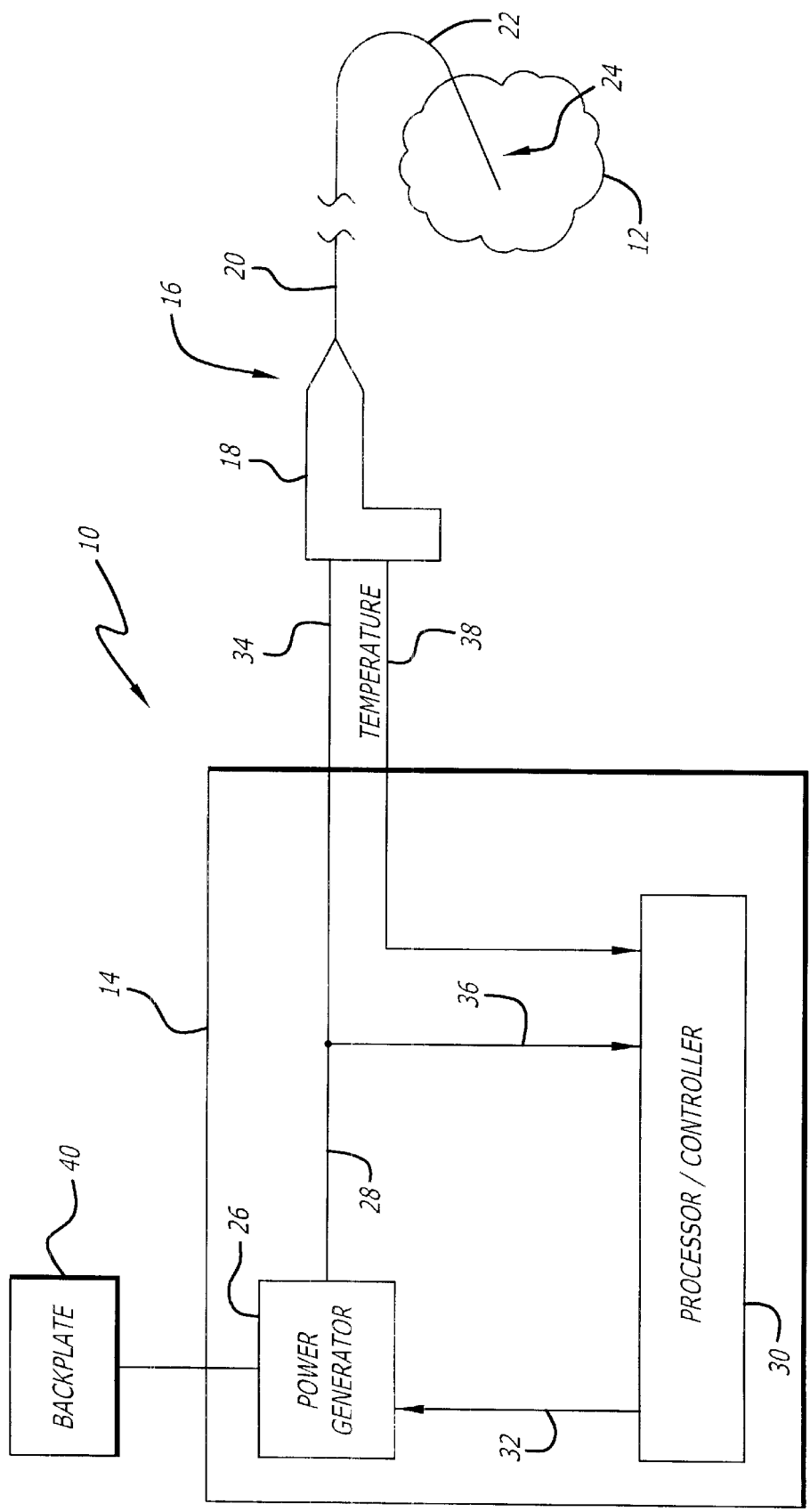
FIG. 1 is a schematic block diagram of an ablation system configured in accordance with aspects of the invention including a power control system ("PCS") and a catheter system.

Turning now to the drawings, in which like reference numerals are used to designate like or corresponding elements among the several figures, in FIG. 1 there is shown a system 10 for use in ablation therapy of a biological site 12, e.g., the atrium or ventricle of the heart. The system 10 includes a power control system 14 and a catheter system 16. The catheter system 16 includes a handle 18 and a steerable catheter sheath 20 having a distal segment 22. The distal segment 22 carries an electrode system 24 and is capable of being percutaneously introduced into the biological site 12.

The power control system 14 includes a power generator 26, that may have any number of output channels through which it provides power or drive signals 28. Power signals 28 are output to the catheter system 16 over lead lines 34 passing through an interconnect cable (not shown) and the catheter sheath 20. Operation of the power generator 26 is controlled by a processor/controller 30 which outputs control signals 32 to the power generator 26. The processor/controller 30 monitors the voltage and current of the power signals 28 over power monitor lines 36. The processor/controller 30 also monitors the temperature at the electrode system 24 over temperature monitor lines 38 which also pass through the interconnect cable and the catheter sheath 20. The system 10 may further include a backplate 40. The backplate 40 is connected to the power generator 26 and generally provides a return path for the power signal 28 delivered to the biological site 12 through the catheter system 16.

As shown in FIGS. 2 and 3a, the distal segment 22 of the catheter system 16 includes an electrode system 24 (FIG. 3). The electrode system 24 is shown in schematic form with the components drawn in more detail to more clearly illustrate the relationship between the components. A preferred embodiment of the electrode system 24 includes six band electrodes 42 arranged in a substantially linear array along the distal segment 22 of the catheter sheath 20. In another embodiment, there are twelve electrodes in the electrode system. The electrode system 24 may include a tip electrode 44. The band electrodes 42 are arranged so that there is a space 46 of non-conductive material between adjacent electrodes. The non-conductive material is provided by the catheter sheath 20. In one configuration of the electrode system 24, the width of the band electrodes 42 is 3 mm and the space 46 between the electrodes is 4 mm.

Figure 3B:
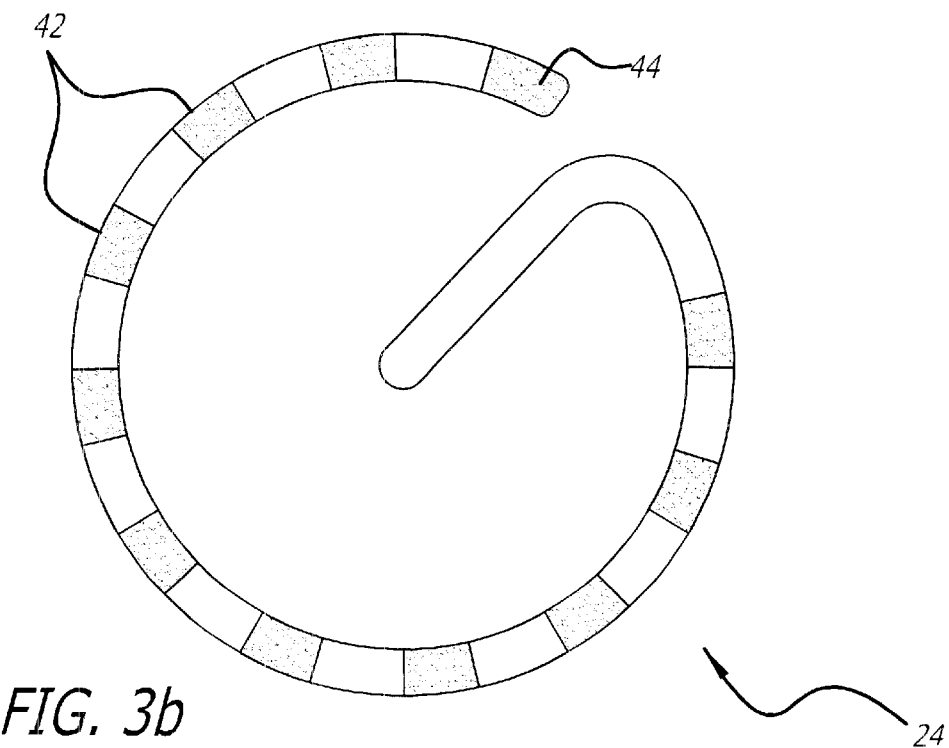
FIG. 3b is a diagram of another configuration of the electrode system of FIG. 2 having a tip electrode and several band electrodes arranged in a circular loop.
Figure 3C:
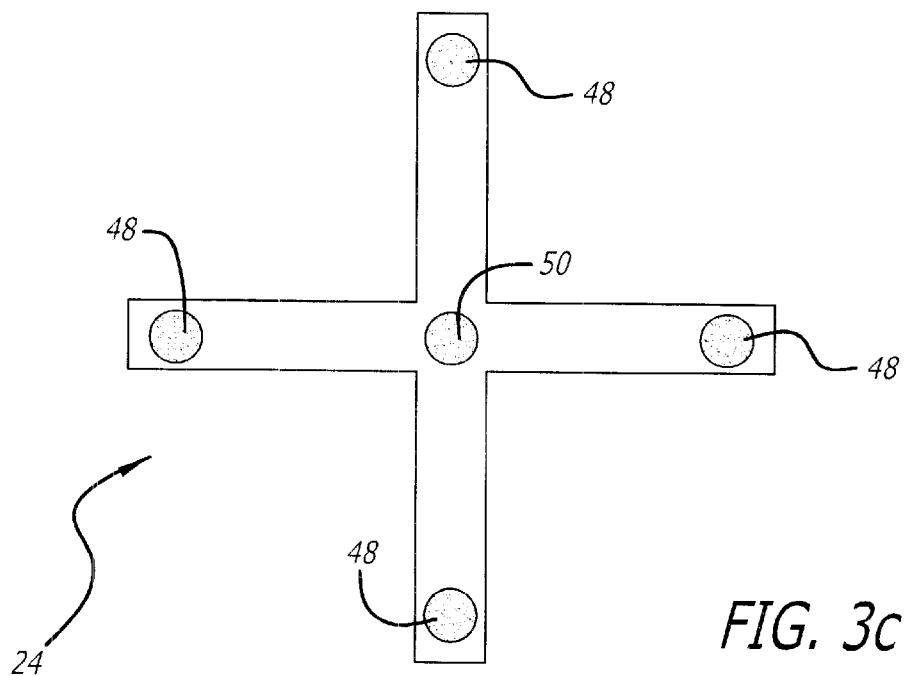
FIG. 3c is a diagram of another configuration of the electrode system of FIG. 2 having a central electrode and four orthogonally arranged branch electrodes.

The arrangement of the electrodes 42, 44 is not limited to a linear array and may take the form of curvilinear arrays or other patterns. For example, as shown in FIG. 3b, the tip electrode 44 and the band electrodes 42 may be arranged in a circular loop. Alternatively, as shown in FIG. 3c, the electrode system 24 may include several branch electrodes 48 orthogonally arranged around a central electrode 50, such as that disclosed in U.S. Pat. No. 5,383,917. A substantially linear or curvilinear array is preferred for certain therapeutic procedures, such as treatment of atrial fibrillation, in which linear lesions of typically 4 to 8 cm in length are desired.

The band electrodes 42 are formed of a material having a significantly higher thermal conductivity than that of the biological tissue to be ablated. Possible materials include silver, gold, chromium, aluminum, molybdenum, tungsten, nickel, platinum, and platinum/10% iridium. Because of the difference in thermal conductivity between the band electrodes 50 and the tissue, the electrodes cool off more rapidly in the flowing fluids at the biological site. The band electrodes 42 are sized so that the surface area available for contact with fluid in the heart, e.g., blood, is sufficient to allow for efficient heat dissipation from the electrodes to the surrounding blood. In a preferred embodiment, the band electrodes 42 are 7 French (2.3 mm in diameter) with a length of 3 mm and a thickness in the range of about 0.002 mm to about 0.010 mm.

Associated with the electrode system 24 are thermal sensors 52 for monitoring the temperature of the electrode system 24 at various points along its length. In one embodiment, each electrode 42, 44 has a thermal sensor 52 mounted to it. Each thermal sensor 52 provides a temperature signal (FIG. 1) to the processor/controller 30 which is indicative of the temperature of the respective band electrode 42 (FIGS. 2 and 3) at that sensor. In another embodiment of the electrode system 24 a thermal sensor 52 is mounted on every other band electrode 42. Thus for a catheter having twelve electrodes, there are thermal sensors on six electrodes. In yet another embodiment of the electrode system 24 the odd numbered electrodes have one thermal sensor 52 while the even numbered electrodes have two thermal sensors. In FIG. 3a, which shows an embodiment having one thermal sensor for each electrode, there is shown a power lead 34 for each electrode 42, 44 to provide power to each electrode for ablation purposes and two temperature leads 38 for each thermal sensor 52 to establish a thermocouple effect. In another configuration (not shown), the power lead acts as one of the thermocouple leads thereby reducing the number of wires. Details of such configurations are disclosed in U.S. Pat. Nos. 6,042,580, 6,045,550 and 6,049,737 which are hereby incorporated by reference. In alternate embodiments, the thermal sensors 52 may include thermistors, RTDs and fluoroptic probes.

Referring now to FIG. 4, a block diagram of a multichannel power control system 14 for use with a catheter system having a plurality of ablation electrodes 42 is shown. Although only three complete channels are shown, the system may comprise more as indicated by the successive dots. Those channels are not shown in FIG. 4 to preserve clarity of illustration. The power generator 26 is configured to provide a power signal 28 to the electrodes 42 in a manner that allows for both unipolar and bipolar application of energy through the biological tissue. To this end, the power generator 26 includes a plurality of output channels each of which produces its own power output signal 28 ($28_1$, $28_2$ through $28_N$ where "n" is the total number of channels). In a preferred embodiment, each output signal 28 is typically a 500 kHz continuous sine wave with a controllable peak-to-peak voltage that is controlled by power control signals 32 provided by the processor/controller 30. The power signals 28 are typically in phase with each other. In an alternate embodiment, each power signal 28 has an associated duty cycle having alternating instances of peak power, i.e., "on" periods, and very low or zero power, i.e., "off" periods. The power signal 28 also has a variable duty cycle for controlling the length of the on periods and off periods. The duty cycle is also controlled by power control signals 32 provided by the processor/controller 30.

Figure 5:
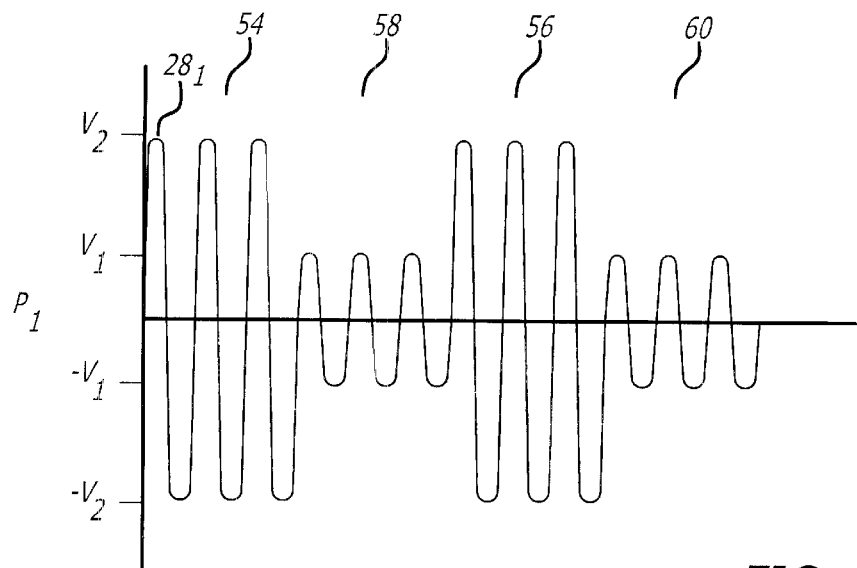
FIGS. 5 and 6 depict first and second continuous power waveforms respectively, each having alternating time periods of high and low peak-to-peak amplitudes.
Figure 6:
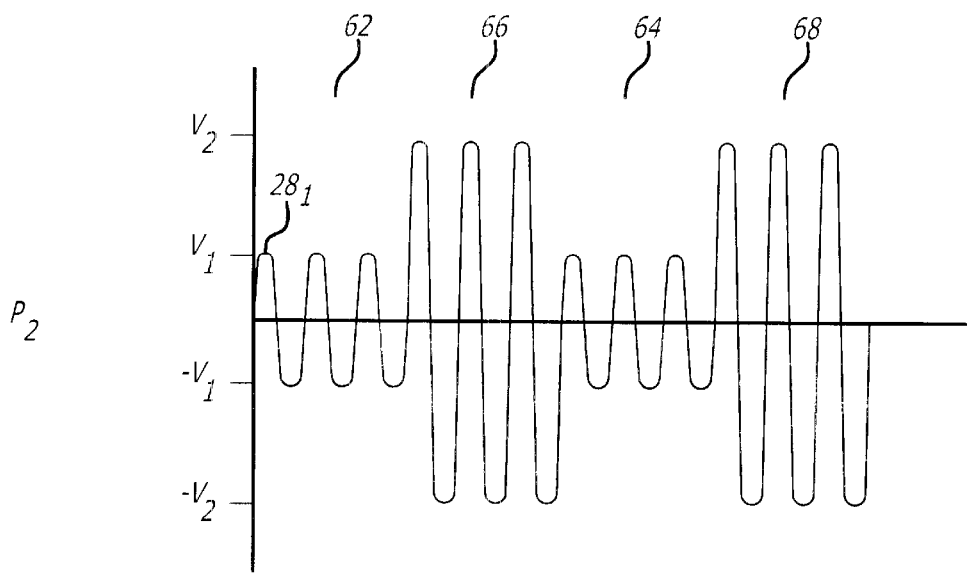

Referring now to the two exemplary power signals $28_1$ and $28_2$ depicted in FIG. 4, each of the signals, shown in detail in FIGS. 5 and 6 as P1 and P2 respectively, has several adjacent time periods (54, 58, 56 and 60 for P1 and 62, 66, 64 and 68 for P2) during which the peak-to-peak voltages of the power signals alternate between first and second substantially constant peak-to-peak amplitudes. Although the time periods within the individual signals are shown to be substantially equal, they may be of different duration. For example, the first time period 54 of signal P1 may be longer or shorter than the second time period 58. Likewise, corresponding time periods between signals may also be different. For example, the first time period 54 of signal P1 may be longer or shorter than the first time period 62 of signal P2. In this situation, the transition between time periods within one signal may occur at a different time then the transition between time periods within another signal.

With specific reference to FIG. 5, during its first time period 54 and third time period 56 power signal P1 has a substantially constant peak-to-peak amplitude V2. During the second time period 58 and fourth time period 60 the peak-to-peak amplitude of the signal has a substantially constant peak-to-peak amplitude V1, different from the peak-to-peak amplitude V2. Likewise, with reference to FIG. 6, during its first time period 62 and third time period 64 power signal P2 has a constant peak-to-peak amplitude V1 that is different from the peak-to-peak amplitude V2 during the second time period 66 and fourth time period 68. Although the respective V1 and V2 peak-to-peak amplitudes for power signals P1 and P2 are the same in FIGS. 5 and 6, they may be different. During each time period, the relative peak-to-peak amplitudes of the power signals P1 and P2 are different thereby establishing bipolar current flow between electrodes E1 and E2.

Figure 7:
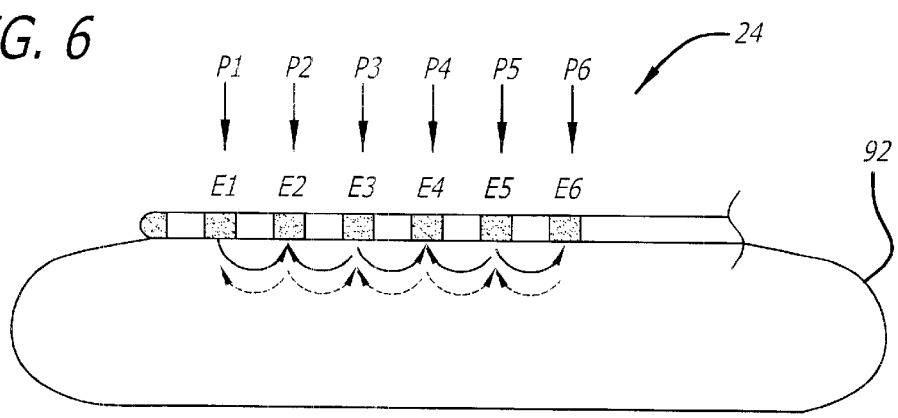
FIG. 7 depicts the distal segment of the catheter of FIG. 2 positioned against biological tissue and the bipolar current paths through the tissue resulting from the application of the power signals of FIG. 5 to electrodes E1, E3 and E5 and the power signals of FIG. 6 to electrodes E2, E4 and E6.

The power generator 26 provides individual power signals 28 to each of the electrodes 42, as such, the bipolar current flow between electrodes may be controlled to obtain lesions of various lengths. For example, with reference to FIG. 7, for an electrode system 24 having six band electrodes E1–E6 positioned proximal to a biological tissue area 92, a long linear lesion may be obtained by providing power signals 28 to the electrodes such that a voltage potential exists between adjacent electrodes. More specifically, electrodes E1, E3 and E5 may be provided with a power signal P1, P3 and P5 such as that shown in FIG. 5 while electrodes E2, E4 and E6 receive a power signal P2, P4 and P6 as shown in FIG. 6. In this situation, current flows from the odd electrodes to adjacent even electrodes as indicted by the solid lines during odd time periods, e.g., first, third, fifth, etc., while current flows from the even electrodes to the odd electrodes as indicted by the dashed lines during even time periods, e.g., second, fourth, sixth, etc. Alternating the direction of current flow in this manner ensures a uniform lesion. In addition, high RF voltages are known to interfere with temperature measurements. By alternating each electrode through an RF "on", or "high", time period and an RF "off", or "low", time period, accurate temperature measurements during the off period are ensured.

As previously mentioned, the duration of the time periods may vary. For example, the processor/controller 30 may be programmed to switch between odd and even time periods anywhere from every two milliseconds to several seconds. While a time period of two milliseconds may be adequate for temperature measurement, longer time periods may be necessary to ensure adequate tissue cooling.

While in the preceding description each time period is assigned a different number, i.e., first, second, third, fourth, etc., the time periods may more conveniently be described as alternating first and second time periods, where the first time periods comprise the odd time periods (first, third, fifth, etc.) and the second time periods comprise the even time periods (second, fourth, sixth, etc.).

For an electrode system 24 having more electrodes 42 than available power output channels, the electrodes may be grouped together in electrode sets, with each electrode in the set receiving the same power signal 28. Depending on the number of output channels and electrodes 42, it is possible for an electrode set to include only one electrode. Alternatively, several electrodes 42 in an electrode system 24, for example, every other electrode in a linear array, may receive independent power signals having substantially the same frequency, phase and peak-to-peak amplitude characteristics. These groups of electrodes may also be described as electrode sets.

With reference to FIG. 4, the temperature signals 38 provided by the electrode thermal sensors 52 (FIG. 3a) are used by the processor/controller 30 to monitor the electrodes 42 for unacceptable temperature conditions. Such conditions are described in detail in U.S. application Ser. No. 09/738, 032, the disclosure of which is hereby incorporated by reference. For example, in one configuration of the system, if the measured temperature at the interface between the tissue and an electrode 42 is between 5° C. and 9° C. greater than a target temperature programmed in the processor/ controller 30, a control signal 32 is sent to the power generator 26 to reduce the peak-to-peak amplitude of the power signal 28 being sent to the particular electrode to allow the electrode-tissue interface temperature to cool off. Once the interface is cooled off, the processor/controller 30, may if necessary, incrementally increases the peak-to-peak amplitude of the power signal 28, thereby increasing the power to the electrode 42 until the electrode-tissue interface temperature settles to a temperature near the target temperature.

In general, the processor/controller is programmed to control the power such that the closer the electrode-tissue interface temperature is to the target temperature the lesser the rate of change of the peak-to-peak amplitude of the power signal 28. For example, if the measured temperature is 20° C. less than the target temperature, the peak-to-peak amplitude may be set relatively high in order to increase the electrode-tissue interface temperature rapidly. As the measured temperature increases and the difference between it and the target temperature becomes smaller, the peak-to-peak amplitude may be reduced in order to settle in on the target temperature and to avoid exceeding the target temperature by a predetermined amount.

Figure 8:
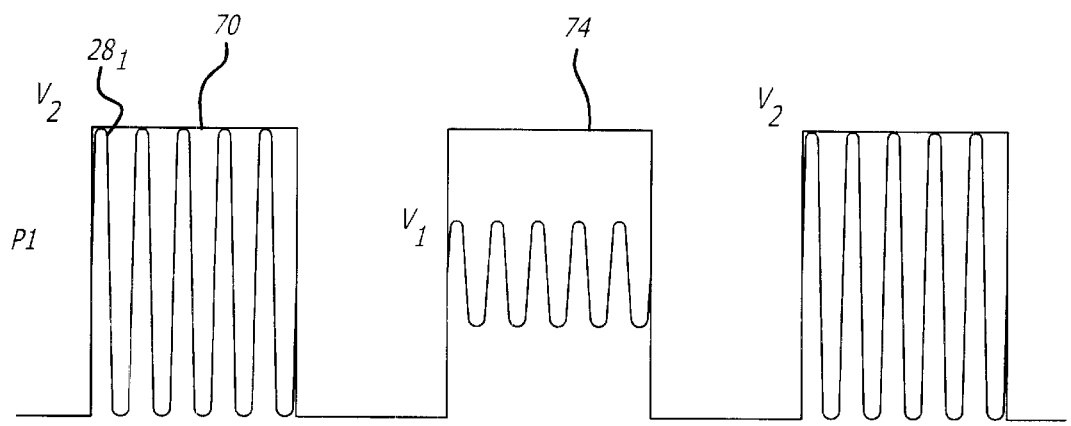
FIGS. 8 and 9 first and second duty-cycled power waveforms respectively, each having alternating on and off periods, with the on periods having alternating high and low peak-to-peak amplitudes.
Figure 9:
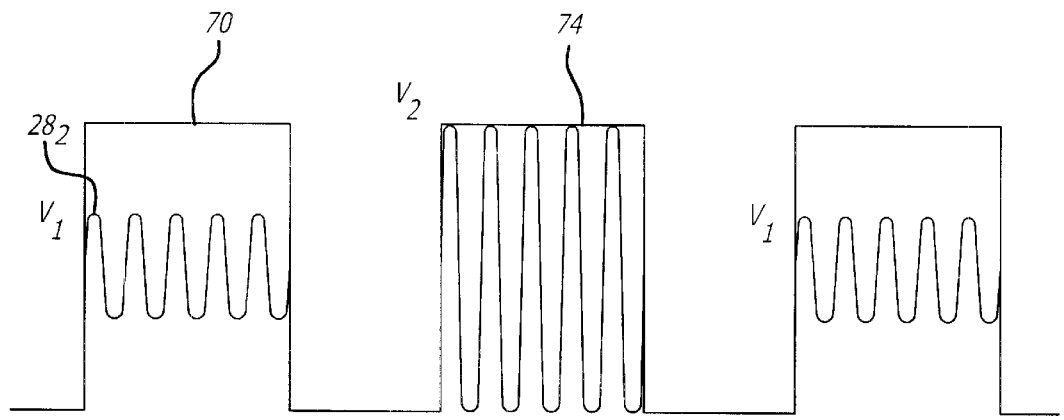

As previously mentioned, as an alternative to a continuous waveform, the power signals 28 may have an associated duty cycle with alternating on and off periods. With reference to FIG. 8, during the first on period 70 of its duty cycle, power signal P1 is maintained at a substantially constant peak-to-peak voltage V2 while, as shown in FIG. 9, power signal P2 is maintained at a substantially constant peak-to-peak voltage V1 which is less than V2 during its first on period 72. During the next on periods 74, 76 of their respective duty cycles, P1 is at an amplitude less than P2. During subsequent on periods, the amplitudes of the power signals P1 and P2 change again, thereby periodically reversing the direction of current flow between adjacent electrodes. In a preferred embodiment of the invention, switching of power signal amplitudes occurs during off periods of the duty cycle.

The use of a duty-cycled power signal 28 provides an alternative to the previously mentioned amplitude-control method of reducing power delivery to an electrode 42. Under a duty-cycle-control method, the power to an electrode 42 may be reduced by reducing the time duration of the on periods of the duty-cycled power signal 28.

The bipolar ablation system thus described is adapted to produce continuous shallow lesions, e.g., approximately 3–4 mm deep. Such lesions may be adequate for procedures within most of the atrium of the heart. However, for procedures within the ventricle, and certain thick areas of the atria, such as the isthmus region, continuous transmural lesions are usually required. In order to produce these lesions both unipolar and bipolar currents are usually required.

Figure 10:
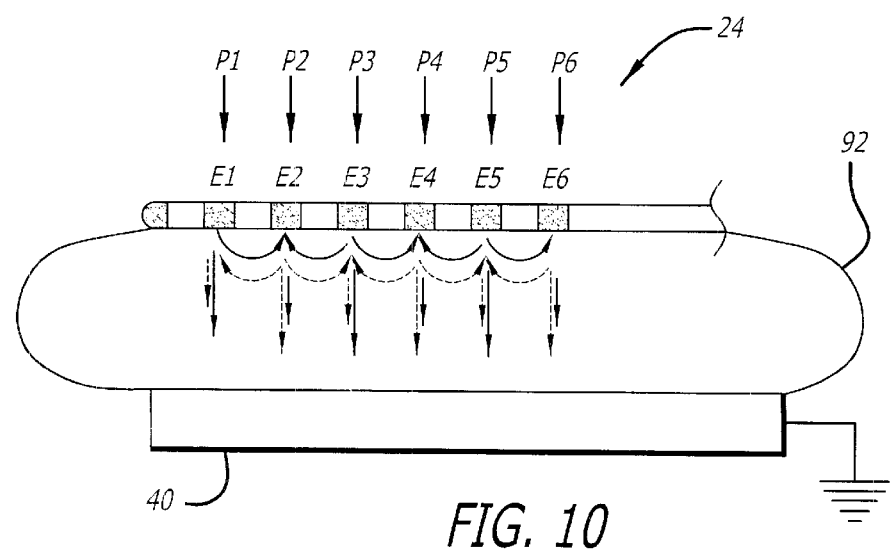
FIG. 10 depicts the distal segment of the catheter of FIG. 2 positioned against biological tissue along with a backplate and the unipolar and bipolar current paths through the tissue resulting from the application of the power signals of FIG. 5 to electrodes E1, E3 and E5 and the power signals of FIG. 6 to electrodes E2, E4 and E6.

In another ablation system configured in accordance with the invention, a backplate 40 is used in conjunction with the electrode system 24 and the power control system 14 to create unipolar current between the electrode system and the backplate and bipolar current between electrodes 42. With reference to FIG. 10, in this configuration, the electrode system 24 is positioned proximal to a biological tissue area 92 within a biological site. A backplate 40 is positioned about the biological site such that the biological tissue is interposed between the electrodes E1–E6 and the backplate. The backplate is maintained at a reference voltage different then the peak-to-peak amplitude of any of the power signals 28, preferably by connecting the backplate to ground. Power signals P1–P6 similar to those previously described with reference to FIGS. 5 and 6 or 8 and 9 are applied to the electrodes such that during a first time period/on period, and subsequent odd time periods/on periods, current flows between adjacent electrodes and between the electrodes and the backplate 40. This current flow is indicated by the solid lines. It is noted that, due to their receipt of a power signal $28_1$ with a larger peak-to-peak amplitude, a greater amount of current flows from the odd electrodes E1, E3 and E5 to the backplate 40 during the first time period than from the even electrodes E2, E4 and E6. This is shown figuratively by the longer solid lines leading from the odd electrodes to the backplate 40.

During a second time period/on period, the amplitudes of the power signals P1–P6 are changed such that the power signals $28_2$ received by the even electrodes E2, E4 and E6 have a larger peak-to-peak amplitude than the power signals $28_1$ received by the odd electrodes E1, E3 and E5. As such, the direction of bipolar current flow reverses and the amount of unipolar current flowing from the even electrodes is greater than that flowing from the odd electrodes. This current flow is indicated by the dashed lines. As previously mentioned, the duration of the time periods may vary. For example, the processor/controller 30 may be programmed to switch between odd and even time periods anywhere from every two milliseconds to several seconds. While a time period of two milliseconds may be adequate for temperature measurement, longer time periods may be necessary to ensure adequate tissue cooling. By periodically switching the amplitudes of the power signals 28 over a period of time, the cumulative current density between the electrodes and the backplate is substantially the same for each electrode. Furthermore, when a backplate is present, alternating the electrodes between high and low voltages ensures that the unipolar current is maintained at each electrode.

Figure 11:
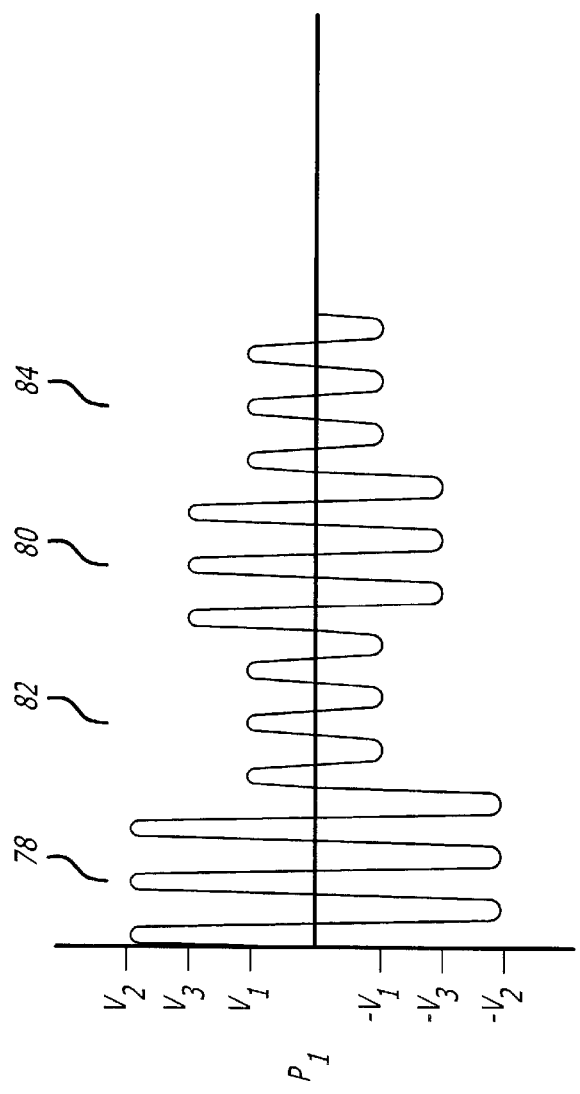
FIG. 11 depicts a continuous power waveform having alternating time periods of high and low peak-to-peak amplitudes, with the high peak-to-peak amplitudes varying.
Figure 13:
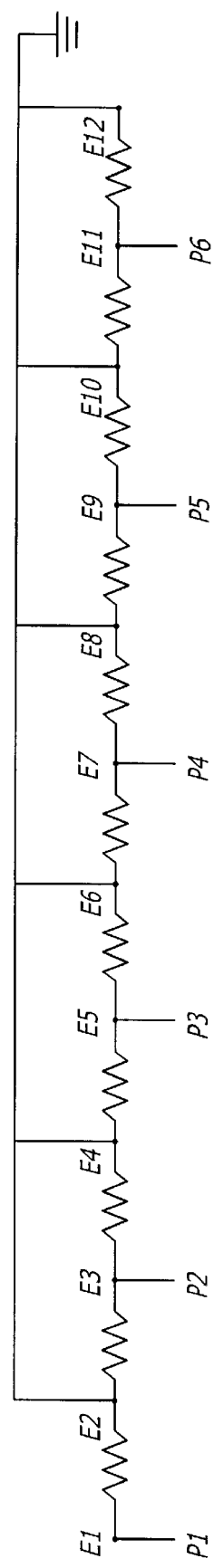
FIG. 13 is a schematic depiction of multi-channel ablation system operating in conjunction with an electrode system wherein the number of electrodes exceeds the number of available power output channels.

In addition to alternating between high and low peak-to-peak amplitudes during consecutive time periods of a continuous wave or on-periods of a duty-cycled wave, the high and or low peak-to-peak amplitude of a power signal may itself change. For example, as shown in FIG. 11, during a first "high" time period 78 the peak-to-peak amplitude of a power signal may be at a first level V2 while during a second "high" time period 80 it is at a second level V3 less than the first level, but still greater than the peak-to-peak amplitude during the "low" time periods 82, 84.

By varying the amplitudes of the power signals a greater degree of control over both unipolar and bipolar current is obtained. For example, by increasing the difference in peak-to-peak amplitude between the power signals applied to electrodes, the level of bipolar current flow between the electrodes increases. The amplitude of either one of the power signals may be varied to change the bipolar current. With reference to FIG. 10, the power signals to electrodes E2, E4 and E6 may be maintained at a constant amplitude while the power signals to electrodes E1, E3 and E5 may be set to any one of several levels. The difference between the amplitudes defines the level of bipolar current.

Figure 12:
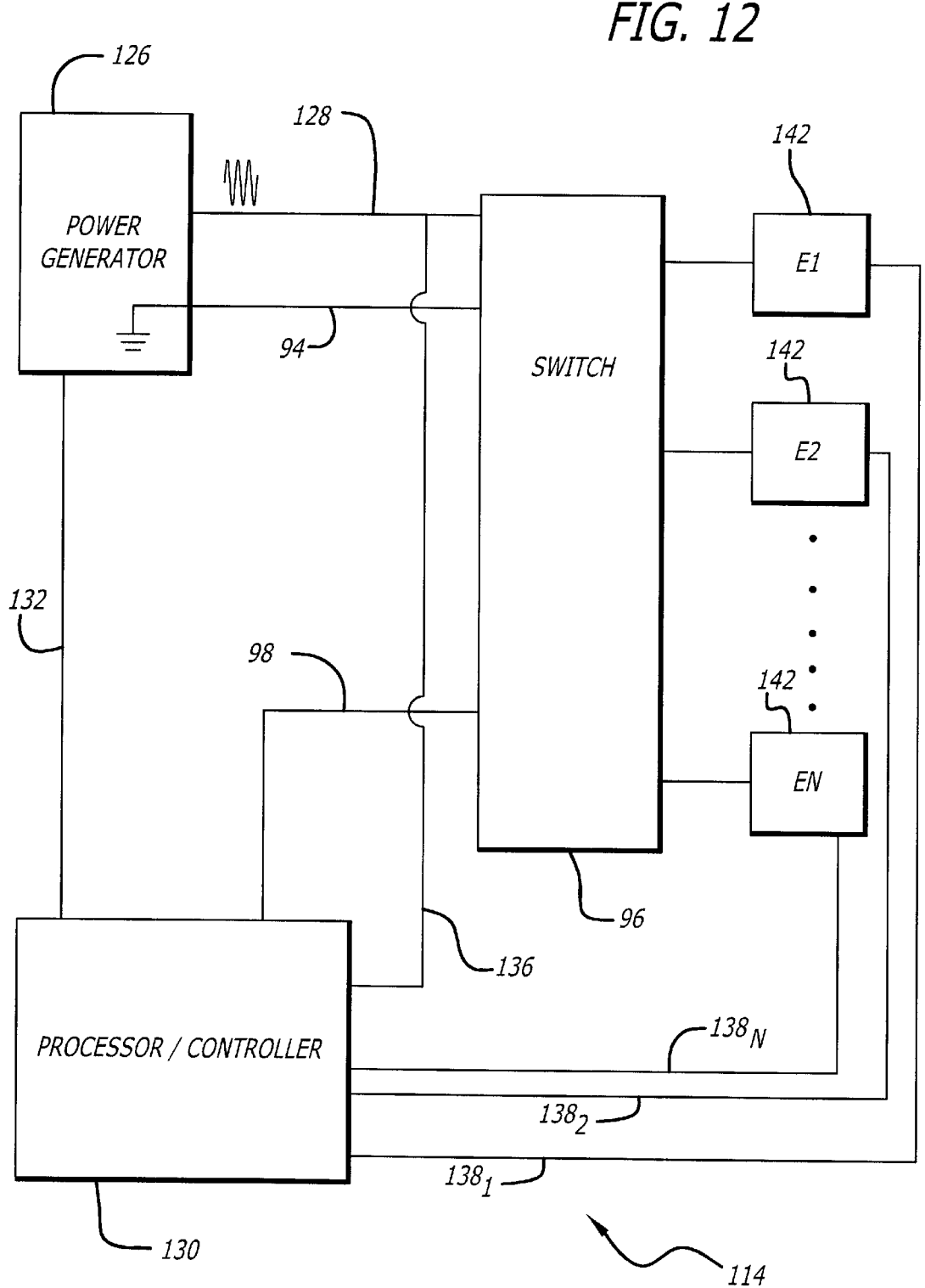
FIG. 12 is a detailed block diagram of another configuration of the power control system of FIG. 1 employing a single-channel power generator.

The foregoing description of an ablation system configured in accordance with the invention has focused on multi-channel power generators, such as that shown in FIG. 4. In another aspect of the invention, a single channel power generator is used. With reference to FIG. 12, a block diagram of a single-channel power control system 14 for use with a catheter system having a plurality of ablation electrodes 42 is shown. The power generator 126 is configured to provide a power signal 128 and a return path 94 to a switch 96. In a preferred embodiment, the power signal 128 is typically a 500 kHz continuous sine wave with a controllable peak-to-peak voltage that is controlled by power control signals 132 provided by the processor/controller 130. In an alternate embodiment, the power signal 128 has an associated duty cycle having alternating on and off periods. The power signal 128 also has a variable duty cycle for controlling the length of the on periods and off periods. The duty cycle is also controlled by power control signals 132 provided by the processor/controller 130.

The processor/controller 130 controls the operation of the switch 96 through switch control signals 98 such that for individual periods of time, potential differences are established between electrodes pairs sequentially along the electrode system 24. For example, in one configuration, the processor/controller 130 is programmed to control the switch 96 so that the power signal 128 is applied to electrode E1 while electrode E2 is tied to the return 94 for a period of time. Bipolar current flow is thus established between electrodes E1 and E2. Next, during another period of time the switch 96 is controlled so that electrode E3 receives the power signal 128 while electrode E2 remained tied to the return 94. Thus current flows between electrodes E2 and E3. Next, the switch is controlled so that electrode E4 is tied to the return 94 while electrode E3 continues to receive the power signal 128, thereby establishing current flow between electrodes E3 and E4. The processor/controller 130 continues this switching process along the electrodes array so that current flows between E4 and E5 and electrodes E5 and E6. For example, the processor/controller 30 may be programmed to switch electrode pairs anywhere from every two milliseconds to several seconds. While a time period of two milliseconds may be adequate for temperature measurement, longer time periods may be necessary to ensure adequate tissue cooling. Once the end of the array is reached, the ablation sequence may be repeated until the desired lesion characteristic is established.

In the foregoing configuration, each pair of adjacent electrode pairs comprises a common electrode. For example, electrode pair E1–E2 and electrode pair E2–E3 have a common electrode E2. During sequential ablation using these adjacent electrode pairs, the common electrode E2 remains tied to the return 94 while the signal applied to E1 is switched to E3. Thus only one switch occurs during the ablation process involving three electrodes. In an alternate configuration, the processor/controller 130 may control the switch 96 so that common electrode E2 does not remain at the same potential through the ablation process. In this case, the power signal applied to electrode E1 is switched to electrode E2 while electrode E3 is tied to the return 94.

As previously mentioned with respect to the multichannel configuration of the invention, the peak-to-peak amplitude of the power signal 128 may be varied in order to control electrode temperature. For example, if after the first sequence of ablation, electrode E5 provides a temperature signal 138 indicative of overheating while each of the remaining electrodes does not, the processor/controller 130 may command the power generator 126 to lower the peak-to-peak amplitude of the power signal when the power signal is switched back to electrode E5 during the next ablation sequence. Alternatively, for a duty-cycled power signal, power maybe reduced by reducing the duty cycle. The remaining electrodes 142 would continue to have the original power signal applied.

In another embodiment, a backplate (not shown) may be added to the ablation system in order to provide a unipolar current path for the electrodes 142. Due to the presence of two return electrodes, i.e., the backplate and the electrode tied to ground, the peak-to-peak amplitude of the power signal 128 may have to be increases to maintain the current density required for effective ablation.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. An ablation system comprising:
   a catheter having a plurality of electrodes;
   a power generator adapted to provide power signals to the electrodes;
   a processor programmed to control the power generator such that:
      during a first period of time, a first peak-to-peak amplitude signal is provided to at least one electrode defining a first electrode set and a second peak-to-peak amplitude signal is provided to at least one electrode defining a second electrode set, wherein the first amplitude is greater than the second amplitude; and
      during a second period of time, a third peak-to-peak amplitude signal is provided to the first electrode set and a fourth peak-to-peak amplitude signal is provided to the second electrode set, wherein the third amplitude is less than the fourth amplitude.

2. The system of claim 1 wherein the first amplitude signal and the third amplitude signal are provided by a first RF power signal.

3. The system of claim 2 wherein the first RF power signal is continuous.

4. The system of claim 2 wherein the first RF signal has a duty cycle with alternating on and off periods.

5. The system of claim 4 wherein the transition between the first and third peak-to-peak amplitudes occurs during an off period of the duty cycle.

6. The system of claim 1 wherein the second amplitude signal and the fourth amplitude signal are provided by a second RF power signal.

7. The system of claim 6 wherein the second RF power signal is continuous.

8. The system of claim 6 wherein the second RF signal has a duty cycle with alternating on and off periods.

9. The system of claim 8 wherein the transition between the second and fourth peak-to-peak amplitudes occurs during an off period of the duty cycle.

10. The system of claim 1 wherein the duration of the first and second times periods are substantially the same.

11. The system of claim 1 wherein the first amplitude signal and the third amplitude signal are provided by a firs: RF power signal, the second amplitude signal and the fourth amplitude signal are provided by a second RF power signal and the first and second RF power signals are in phase.

12. The system of claim 1 wherein the processor is further programmed to control the power generator such that there are a plurality of alternating first and second time periods.

13. The system of claim 1 wherein the processor is further programmed to adjust the duration of the first and second time periods.

14. The system of claim 1 wherein the processor is programmed to vary a bipolar current between electrodes by varying any one of the first, second, third and fourth amplitudes from time period to time period.

15. The system of claim 1 further comprising a backplate, wherein the power generator is adapted so maintain the backplate at a reference voltage different then the peak-to-peak amplitude of any one of the first, second, third and fourth amplitudes.

16. The system of claim 1 wherein the plurality of electrodes are arranged in either of a linear array and curvilinear array and the first electrode set comprises every other electrode and the second electrode set comprises the remaining electrodes.

17. The system of claim 1 wherein the electrodes are arranged in an orthogonal array having a central electrode and a plurality of branch electrodes and the first electrode set comprises the central electrode and the second electrode set comprises the branch electrodes.

18. The system of claim 1 wherein:
at least one electrode in each electrode set comprises a temperature sensor adapted to provide signals indicative of the temperature at the electrode to the processor; and
the processor is programmed to convert the temperature signals to a temperature reading, compare the temperature reading to a target temperature and adjust the power provided by the power signal based on the difference between the temperature reading and the target temperature.

19. The system of claim 18 wherein when the temperature reading is greater than the target temperature by a predetermined amount, power is reduced.

20. The system of claim 19 wherein the power is reduced by reducing the peak-to-peak amplitude of the power signal.

21. The system of claim 19 wherein the power signal has an associated duty cycle and the power is reduced by reducing the duty cycle.

22. The system of claim 18 wherein when the temperature reading is less than the target temperature by a predetermined amount, power is increased.

23. The system of claim 22 wherein the power is increased by increasing the peak-to-peak amplitude of the power signal.

24. The system of claim 22 wherein the power signal has an associated duty cycle and the power is increased by increasing the duty cycle.

25. The system of claim 22 wherein power is increased incrementally.

26. A system for delivering energy to biological tissue associated with a biological site, said system comprising:
a catheter carrying an electrode system having a plurality of electrodes at its distal end, the electrode system adapted to be positioned proximal to the biological tissue;
a backplate adapted to be positioned proximal to the biological site so that the biological tissue is interposed between the electrode system and the backplate;
a power control system programmed to:
during a first period of time, provide a first peak-to-peak amplitude signal to at least one electrode defining a first electrode set and a second peak-to-peak amplitude to at least one electrode defining a second electrode set, wherein the first amplitude is greater than the second amplitude of,
during a second period of time, provide a third peak-to-peak amplitude signal to the first electrode set and a fourth peak-to-peak amplitude signal to the second electrode set,
wherein third amplitude of the third power is less than the fourth amplitude; and
the during at least one of the first and second time periods, establishing a voltage potential between the backplate and either of the first and second electrode sets.

27. The system of claim 26 wherein the first amplitude signal and the third amplitude signal are provided by a first continuous RF power signal and the second amplitude signal and the fourth amplitude signal are provided by a second continuous RF power signal.

28. The system of claim 27 wherein the first and second RF power signals are in phase.

29. The system of claim 28 wherein the transition from the first peak-to-peak amplitude to the third peak-to-peak amplitude and from the second peak-to-peak amplitude to fourth peak-to-peak amplitude occurs at about the same time.

30. The system of claim 26 wherein the first amplitude signal and the third amplitude signal are provided by a first duty-cycled RF power signal and the second amplitude signal and the fourth amplitude signal are provided by a second duty-cycled RF power signal.

31. The system of claim 30 wherein the transition from the first peak-to-peak amplitude to the third peak-to-peak amplitude and from the second peak-to-peak amplitude to the fourth peak-to-peak amplitude occurs during an off period of the duty cycle.

32. The system of claim 26 wherein the power control system is further programmed to control the power generator such that there are a plurality of alternating first and second time periods.

33. The system of claim 26 wherein the power control system is further programmed to adjust the duration of the first and second time periods.

34. The system of claim 26 wherein the power control system is further programmed to vary the bipolar current between electrodes by varying any one of the first, second, third and fourth amplitudes from time period to time period.

35. A power control system for delivering energy to a biological tissue interposed between a plurality of electrodes, said power control system comprising:
a power generator adapted to provide power signals;
a processor programmed to control the power generator such that:
during a first period of time, a first peak-to-peak amplitude signal is adapted to be provided to at least one electrode defining a first electrode set and a second peak-to-peak amplitude signal is adapted to be provided to at least one electrode defining a second electrode set, wherein the first amplitude is greater than the second amplitude; and
during a second period of time, a third peak-to-peak amplitude signal is adapted to be provided to the first electrode set and a fourth pea-to-peak amplitude signal is adapted to be provided to the second electrode set, wherein the third amplitude is less than the fourth amplitude.

36. A method of delivering energy to biological tissue associated with a biological site, said method comprising:
positioning a catheter having a plurality of electrodes proximal to the biological tissue;
providing a power control system programmed to:
during a first period of time providing a first peak-to-peak amplitude signal to at least one electrode defining a first electrode set and a second peak-to-peak amplitude signal to at least one electrode defining a second electrode set, wherein the first amplitude is greater than the second amplitude; and
during a second period of time, providing a third peak-to-peak amplitude signal to the first electrode set and a fourth peak-to-peak amplitude signal to the second electrode set, wherein the third amplitude is less than the fourth amplitude.

37. The method of claim 36 further comprising repeating the conditions of the first and second time periods for a plurality of alternating subsequent first and second time periods.

38. The method of claim 37 further comprising adjusting the amplitude of any one of the peak-to-peak signals so that during subsequent first and second time periods the voltage potential between the first and second electrode sets is different from the voltage potential between the first and second electrode sets during either of the first and second time periods.

39. The method of claim 36 wherein the first amplitude signal and the third amplitude signal are provided by a first continuous RF power signal, the second amplitude signal and the fourth amplitude signal are provided by a second continuous RF power signal and the transition from the first peak-to-peak amplitude to the third peak-to-peak amplitude and from the second peak-to-peak amplitude to fourth peak-to-peak amplitude occurs at about the same time.

40. The method of claim 36 wherein the first amplitude signal and the third amplitude signal are provided by a first duty-cycled RF power signal, the second amplitude signal and the fourth amplitude signal are provided by a second duty-cycled RF power signal and the transition from the first peak-to-peak amplitude to the third peak-to-peak amplitude and from the second peak-to-peak amplitude to the fourth peak-to-peak amplitude occurs during an off period of the duty cycle.

41. The method of claim 36 further comprising:
positioning a backplate proximal to the biological site so that the biological tissue is interposed between the first and second electrode sets and the backplate; and
maintaining the backplate at a reference voltage different then the peak-to-peak amplitude of any one of the first, second, third and fourth amplitude signals.

42. An ablation system comprising:
a catheter having a plurality of electrode pairs;
a power control system programmed to:
during a first period of time, establish a voltage potential between a first electrode pair by providing a first power signal to one of the electrodes while maintaining the other electrode at a reference potential; and
during a second period of time, establish a voltage potential between a second electrode pair by providing the first power signal to one of the electrodes while maintaining the other electrode at the reference potential.

43. The ablation system of claim 42 wherein the first and second electrode pairs comprise a common electrode and the first power signal is provided to the common electrode during each of the first and second time periods.

44. The ablation system of claim 42 wherein the first pair of electrodes comprises adjacent electrodes.

45. The ablation system of claim 42 wherein the second pair of electrodes comprises adjacent electrodes.

46. The ablation system of claim 42 wherein the power control system is further programmed to, during subsequent time periods, establish a voltage potential between each of the remaining electrode pairs by providing the first power signal to one of the electrodes while maintaining the other electrode at a reference potential.

47. The ablation system of claim 46 wherein the power contra) system is further programmed to repeatedly establish voltage potentials between electrode pairs in sequence from the first electrode pair to the last electrode pair.

48. The ablation system of claim 42 wherein the power control system comprises:
a power generator adapted to output the power signal;
a switch device having an input connected to the power generator for receiving the power signal and a plurality of outputs each individually connected to one of the electrodes, the switch device adapted to selectively couple the power signal to one of the electrodes.

49. The ablation system of claim 48 wherein the power generator is further adapted to provide the reference potential.

50. The ablation system of claim 42 wherein:
at least one electrode in each electrode pair comprises a temperature sensor adapted to provide signals indicative of the temperature at the electrode to the power control system; and
the power control system is adapted programmed to convert the temperature signals to a temperature reading, compare the temperature reading to a target temperature and adjust the power provided by the power signal based on the difference between the temperature reading and the target temperature.

51. The ablation system of claim 50 wherein when the temperature reading is greater than the target temperature by a predetermined amount, power is reduced.

52. The ablation system of claim 50 wherein when the temperature reading is less than the target temperature by a predetermined amount, power is increased.

53. The ablation system of claim 52 wherein power is increased incrementally.

54. A method of delivering energy to biological tissue associated with a biological site, said method comprising:
positioning a catheter having a plurality of electrodes pairs proximal to the biological tissue;
providing a power control system programmed to:
during a first period of time establishing a voltage potential between a first electrode pair by providing a first power signal to one of the electrodes while maintaining the other electrode at a reference potential; and
during a second period of time establishing a voltage potential between a second electrode pair by providing the first power signal to one of the electrodes while maintaining the other electrode at the reference potential.

55. The method of claim 54 wherein the first and second electrode pairs comprise a common electrode and the first power signal is provided to the common electrode during each of the first and second time periods.

56. The method of claim 54 further comprising, during subsequent time periods, establishing a voltage potential between each of the remaining electrode pairs by providing the first power signal to one of the electrodes while maintaining the other electrode at a reference potential.

57. The method of claim 56 further comprising repeatedly establishing voltage potentials between electrode pairs in sequence from the first electrode pair to the last electrode pair.

58. The method of claim 54 further comprising:
sensing the temperature at one of the electrodes within the electrode pair;
comparing the temperature reading to a target temperature; and
adjusting the power provided by the power signal based on the difference between the temperature reading and the target temperature.

59. The method of claim 58 further comprising reducing the power when the temperature reading is greater than the target temperature by a predetermined amount.

60. The method of claim 59 wherein reducing the power comprises reducing the peak-to-peak amplitude of the power signal.

61. The method of claim 59 wherein the power signal has an associated duty cycle and reducing the power comprises reducing the duty cycle.

62. The method of claim 58 further comprising increasing the power when the temperature reading is less titan the target temperature by a predetermined amount.

63. The method of claim 62 wherein increasing the power comprises increasing the peak-to-peak amplitude of the power signal.

64. The method of claim 62 wherein the power signal has an associated duty cycle and increasing the power comprises increasing the duty cycle.

* * * * *

UNITED STATES PATENT AND TRADEMARK OFFICE
CERTIFICATE OF CORRECTION

PATENT NO. : 6,635,056 B2
DATED : October 21, 2003
INVENTOR(S) : Veerichetty A. Kadhiresan et al.

It is certified that error appears in the above-identified patent and that said Letters Patent is hereby corrected as shown below:

Column 16,
Line 15, delete "adapted".

Signed and Sealed this

Twenty-seventh Day of January, 2004

JON W. DUDAS
*Acting Director of the United States Patent and Trademark Office*